United States Patent [19]
Gutierrez

[11] Patent Number: 5,961,981
[45] Date of Patent: Oct. 5, 1999

[54] BIOLOGICALLY-ACTIVE COMPOSITIONS EXTRACTED FROM DICTYOTALES PLANT FAMILY

[76] Inventor: Gilles Gutierrez, 39 rue Lieutenant-Colonel-Prévost, Lyon, France, 69006

[21] Appl. No.: 08/930,365

[22] PCT Filed: Jan. 20, 1997

[86] PCT No.: PCT/FR97/00106

§ 371 Date: Oct. 31, 1997

§ 102(e) Date: Oct. 31, 1997

[87] PCT Pub. No.: WO97/25998

PCT Pub. Date: Jul. 24, 1997

[30] Foreign Application Priority Data

Jan. 18, 1996 [FR] France .................................. 96/00522

[51] Int. Cl.⁶ .................................................. A61K 35/78
[52] U.S. Cl. ............................................................ 424/195.1
[58] Field of Search ............................................ 424/195.1

[56] References Cited

U.S. PATENT DOCUMENTS 5,556,626   9/1996   D'Arrigo ............................ 424/195.1

FOREIGN PATENT DOCUMENTS 0 655 250 A1   5/1995   European Pat. Off. .

OTHER PUBLICATIONS

Okazaki M., A Study of Calcium Carbonate Depostion in the Genus Padina, Br Phycol J 21:217–224, Jun. 1986.

*Primary Examiner*—Ralph Gitomer
*Attorney, Agent, or Firm*—Bierman, Muserlian and Lucas

[57] ABSTRACT

Biological substances and particularly biologically active substances of marine origin are disclosed. The novel biologically active substances are extracts of plants of the dictyotales family and have characteristic analytical properties. A method for preparing said novel substances and pharmaceutical, cosmetic and/or food compositions containing such substances are also disclosed. Said biologically active substances are useful for preparing pharmaceutical, cosmetic and/or food compositions for altering the synthesis of glycosylated elements in the extracellular matrix of human and animal tissues.

2 Claims, No Drawings

BIOLOGICALLY-ACTIVE COMPOSITIONS EXTRACTED FROM DICTYOTALES PLANT FAMILY

The present invention relates to the field of biology, and more precisely to biologically active substances of marine origin.

The present invention relates to new biologically active substances extracted from plants of the family of the Dictyotales, a process for obtaining them and compositions comprising them.

The compositions of the present invention are intended for modification of the synthesis of glycosylated elements of the extracellular matrix (ECM) of animal and human tissues.

The term plants of the family of the Dictyotales is to be understood as meaning, more particularly, those which are capable of fixing, condensing, precipitating or effecting the synthesis, on their thallus, of calcium carbonate in the crystalline form called aragonite.

The term plants may relate to the dried or fresh, ground or untreated plant.

The plants of which the biologically active substances of the invention are extracted are the Pheophyceae, class of the Fucophyceae, order of the Dictyotales, family of the Dictyotaceae. Only some genera belong to the family of the Dictyotales, and these are Padina, Zonaria or Dictyota. The genus Padina comprises the most frequent species. By way of example, it is possible to find on the shore of the Mediterranean Sea the species *pavonica, boyana (P. tenuis)* and *boergesenii*, on the shores of the Pacific (not including the species already mentioned): *arborescens, australis, boryana, caulens, commersonii, concrescens, crasse, durvillei, elegans, fernandeziana, fraseri* and *gymnospora*, and furthermore on the shores of the Atlantic Ocean: *glabra, haitensis, distromatica* and *dubia*. There are also species typical of the Indian Ocean. One of the characteristics of these plants is that of fixing, on their thallus, a layer of calcium carbonate of the aragonite or orthorhombic type on the surface of the fronds. This characteristic is detected by X-ray diffraction analysis of the powder obtained with these plants. X-ray diffraction shows that the powder of these plants has significant intensity peaks at the angles $2\theta$:$-3.393°$, $-3.268°$, $-2.699°$, $-2.682°$, $-2.371°$, $-2.336°$ (doublet), $-1.976°$ and $-1.877°$ (doublet). These diffraction angles are characteristic of aragonite. The present invention relates to new biologically active substances which modify the synthesis of glycosylated elements of the extracellular matrix of animal and human tissues and which are extracted from plants of the family of the Dictyotales. These new biologically active substances are characterized in particular by a polycyclic structure carrying a side chain having 4 to 10 carbon atoms in a straight to or branched line and containing one or two double bonds.

The new substances are also characterized by more precise analytical data.

The present invention also relates to a process for obtaining the biologically active substances extracted from plants of the family of the Dictyotales. In a first stage, the plant of the family of the Dictyotales is subjected, after harvesting, to drying, if possible in the absence of light, to keep its pharmacological properties intact.

Slow drying with significant insolation leads to substances which are not very active and are unstable when being obtained. Drying by more appropriate methods, with the main condition that active substances are obtained, are therefore preferably used.

For this reason, drying of the ground or untreated plants is carried out by ventilation without heating, and a vegetable material of dark maroon colour, on which the white streaks of calcium carbonate contrast vividly, is thus obtained. Another method, although less economical, is also satisfactory: It comprises draining the plants to a high degree and then drying them in the absence of air. Lyophilization of the ground or non-ground plant gives an anhydrous product in an advantageous manner.

These last two techniques give a material of dark green-brown colour which is very fragile and easily reduced to a powder, which facilitates extraction with a solvent to give the biologically active substances.

The advantage of a plant which has been dried to a high degree is that a vegetable material which keeps well (in the absence of moisture) is obtained, from which it will be possible to extract the stabilized or non-stabilized active substance or substances without being impeded by the presence of a polar solvent. Furthermore, completely dried plants are more easily reduced to a powder.

The process for the preparation of the biologically active substances is characterized in that the plant of the family of the Dictyotales is subjected to drying and/or to lyophilization, to grinding, followed by one or more extractions of the vegetable material by an organic solvent chosen from the group consisting of lower alkanols (ethanol . . . ), aliphatic ketones (acetone . . . ), alkanes (pentane, hexane, heptane . . . ), cycloalkanes (cyclohexane . . . ), halogenated solvents (chloroform, methylene chloride . . . ), aromatic solvents, esters (ethyl acetate . . . ), ethers and the like, to give an organic extract of the plant, the organic extract is dried by evaporation of the solvent, the dried organic extract is purified by one or more purification stages carried out successively by liquid/liquid contact, by low pressure or high pressure column chromatography or by high performance liquid chromatography, to give the active substances of plants of the family of the Dictyotales.

The organic solvents can be used by themselves or in combination. Generally, it is possible to use water-miscible organic solvents, as well as all solvents capable of extraction of the active substances from the fronds of the plant. The solvents will preferably be chosen from among the volatile solvents, since it is desirable to obtain the biologically active substances freed from the solvent. In fact, the volatile solvents which dissolve the biologically active substances can be evaporated from a support, such as cellulose or its derivatives, colloidal silica, high molecular weight alkanes, such as paraffins, amphiphilic solvents, such as polyethylene glycol (PEG) or propylene glycol, or also inert products, such as glycerol and the like.

The organic solvents will preferably be acetone or ethanol.

The ratio used is preferably 1 gram of dried vegetable material per 5 ml of solvent, and the contact times between the vegetable material and the organic solvent are preferably 4 to 5 days.

However, during the maceration, very different ratios of dried material with respect to the solvent have been used with good results. The volumes used for the same amount of dried material vary from 1 to 50. Furthermore, the contact times between the organic solvent and the vegetable material vary from 12 hours to 5 days.

Moreover, although more difficult to use, aqueous extraction in an ammoniacal medium gives satisfactory results. To carry out the extraction of the biologically active substances, it is not necessary to macerate the vegetable material in the solvent chosen, and it is possible to pass the solvent continuously over the powder (percolation). It is sufficient to regulate the flow rate and to concentrate the extract to obtain a solution of chosen activity.

In the present case, the plant of the family of the Dictyotales, once dried and/or lyophilized and ground, is subjected to one or more extractions by bringing the plant into contact with acetone for 4 to 5 days in proportions of 1 gram of material per 5 ml of acetone.

The acetone extract obtained is dried by evaporation of the solvent and then purified by the purification stages defined below.

The first purification stage is carried out by liquid/liquid contact. The dried acetone residue or extract is taken up in a methanol/water mixture in contact with hexane. In a second stage, the aqueous-methanolic phase is brought into contact, after concentration and dilution in water, with ether. In this manner, the final ethereal phase is biologically active.

The second purification stage is characterized by low pressure column chromatography. The support used is a gel of the Sephadex LH 20® type. The elution is carried out by a chloroform/methanol gradient. The biologically active fraction is eluted in chloroform/methanol in proportion of 97/3 volume by volume.

During rinsing of the column with a chloroform/methanol 70/30 mixture, a second residual active fraction is eluted.

The following stages of purification take place by semi-preparative high performance liquid chromatography (HPLC). The dimensions of the column are 250 mm (for the length) and 10 mm (for the diameter). The supports used are: $C_{18}$-grafted silica and a diol-grafted silica. The flow rate is 8 ml/min.

On the diol-grafted silica support, with an eluent of hexane/isopropanol 92/8, the active fractions are eluted between 20 and 25 min and 35 and 40 min. On the $C_8$-grafted silica support, with an eluent of acetonitrile/water 85/15, the active fraction is eluted between 15 and 17 min, and with an eluent of acetonitrile/water/acetic acid 85/15/0.05, the active fractions are eluted between 17 and 20 min and 30 and 40 min.

At the end of these purification stages, a biologically active substance of yellow-green colour is obtained.

Various analytical methods (UV, IR, NMR spectra, thin-layer chromatography . . . ) are carried out for characterization of the biologically active substance or substances extracted from plants of the family of the Dictyotales.

The UV spectrum of the final active fraction, recorded in methanol, is characterized by several absorption bands situated at 202 nm, with a shoulder at 228 nm, between 260 and 270 nm, between 400 and 460 nm and at 630 nm.

At the end of these purification stages, thin-layer chromatography (TLC) with chemical development is also carried out (the developing reagents used are sulphuric-acid anisaldehyde, sulphuric-acid vanillin, phosphomolybdate and ethanolic sulphuric acid). After development, the presence of several spots is noted. The frontal retention times are: Rf=0.15 and 0.90, 0.95, and correspond to the biologically active zones originating from preparative TLC carried out under the same conditions, that is to say a TLC plate with diol-grafted silica, elution with hexane/isopropanol 85/15.

The mass spectra, the IR spectra and the proton or [$^{13}$C] NMR spectra have also completed the data as regard the structure of the new biologically-active substances extracted from plants of the family of the Dictyotales according to the invention. In particular, analysis of the 13 carbon NMR spectrum demonstrates the presence of the side chain having 4 to 10 carbon atoms in a straight or branched line and containing one to two double bonds, which is carried by the polycyclic structure.

It has also been possible to obtain the biologically active substances extracted from plants of the family of the Dictyotales by maceration or lixiviation of 1 g of dried vegetable material in 5 ml of pure ethanol for 12 hours. Ethanol is a solvent which is well accepted by the cells and is completely miscible with the aqueous nutrient solutions in which the cells are immerged. The following purification stages were then carried out. High pressure chromatography is carried out over a normal silica column. 20 µl of the biologically active fraction are injected into a high pressure chromatograph and the fraction is then eluted with a heptane/ether mixture (90/10) at a flow rate of 2 ml/min. All the activity of the substances extracted from plants of the family of the Dictyotales is found in the fraction eluted between 6.9 min and 8.5 min. It is possible to carry out high performance liquid chromatography (HPLC) in the same manner. The HPLC column is packed with a $C_{18}$-grafted silica, the eluent is a methanol/water 80/20 mixture and the flow rate is 4 ml/min. All the activity of the extracted substances is then concentrated in the fraction eluted after a retention time of between 16 and 18 min.

The chromatogram obtained with light diffusion detection shows, at this retention time, a certain amount of substance which constitutes the active fraction of the plant provided that the chromatography has been carried out under reduced pressure, such that evaporation of the mobile phase with entrainment of the active fraction does not take place.

The new biologically active substances extracted from plants of the family of the Dictyotales are thus characterized during the purification stages, and if the extractions have been carried out with acetone, by the following analytical data:

retention times in semi-preparative high performance liquid chromatography over a diol-grafted silica support with an eluent of hexane/isopropanol 92/8 of between 20 and 25 min and 35 and 40 min, a retention time in semi-preparative high performance liquid chromatography over a $C_{18}$-grafted silica support with an eluent of acetonitrile/water 85/15 of between 15 and 17 min, retention times in semi-preparative high performance liquid chromatography over a $C_{18}$-grafted silica support with an eluent of acetonitrile/water/acetic acid 85/15/0.05 of between 17 and 20 min and 30 and 40 min.

During the purification stages and if the extractions have been carried out with ethanol, the analytical data are:

a retention time in high pressure chromatography over a normal silica column with an eluent of heptane/ether (90/10) of between 6.9 min and 8.5 min, a retention time in high performance liquid chromatography packed with a $C_{18}$-grafted silica column with an eluent of methanol/water 80/20 of between 16 and 18 min.

The biologically active substances are also characterized after the purification stages, and if the extractions have been carried out with acetone, by the following analytical data:

a UV spectrum in methanol having several absorption bands situated at 202 nm, with a shoulder at 228 nm, between 260 and 270 nm, between 400 and 460 nm, and at 630 nm, a thin-layer chromatography (TLC) having, after chemical development (sulphuric-acid anisaldehyde, sulphuric-acid vanillin, phosphomolybdate, ethanolic sulphuric acid) frontal retention times of 0.15, 0.90 and 0.95.

The substances extracted with the organic solvents are often difficult to handle (evaporation, hydration, risk of deflagration . . . ). It is thus desirable to fix them on a solid support or supports, such as an organic absorbent polymer, such as, for example, cellulose, absorbent minerals or mineral compositions, or absorbents (colloidal silica . . . ), products which are more inert, such as the paraffins, the polyethylene glycols (PEG), the propylene glycols, polyvinylpyrrolidone etc . . . . All the inert supports of low degree of oxygenation are suitable.

The characteristics of the fixed substances can vary greatly according to the conditions of extraction of the substances from plants of the family of the Dictyotales, the fixing material, the stabilization conditions and the material on which the extraction solvent is fixed. The consistency thus varies, and the colour can vary from pure green to maroon.

The present invention also relates to the biologically active substances adsorbed on an inert mineral or organic material and then desolvated.

The biologically active substances according to the invention extracted from plants of the family of the Dictyotales show very interesting pharmacological properties, and as a result are employed in therapeutics, in cosmetics, in nutrition, in human and veterinary dietetics, in implantology and in bone or joint surgery. These substances are intended for use in the form of pharmaceutical, cosmetic and/or nutritional compositions or implants.

The biologically active substances extracted from plants of the family of the Dictyotales are intended for modification of the synthesis of glycosylated elements of the extracellular matrix (ECM) of animal and human tissues. These substances stimulate the synthesis of glycosaminoglycans (GAG) such as hyaluronic acid, chondroitin, chondroitin-sulphuric acids, dermatan-sulphuric acid, heparan-sulphuric acid, heparin and keratan-sulphuric acid, and the synthesis of proteoglycans, such as aggrecan, decorin, biglycan, versican, fibromodulin, fibroglycan, syndecan, betaglycan and glypican.

The biologically active substances according to the invention are thus used in order to prepare compositions intended for modification of the synthesis of glycosylated elements of the extracellular matrix (ECM) of animal and human tissues, and in particular for stimulation of the synthesis of glycosaminoglycans (GAG) and of proteoglycans of the extracellular matrix (ECM) of animal and human tissues.

The substances of the present invention are used in particular in order to prepare cosmetic or dermatological compositions intended for improvement of glycosylated syntheses of glycosaminoglycans and of proteoglycans in the skin.

The substances of the present invention stimulate the protein syntheses and the glycoside syntheses of the cells of connective tissue or of the mesenchyme. The substances are used in order to prepare topical compositions intended for indirect remodelling of the activity of connective or mesenchymal cells by direct action on the epithelial cells.

The substances extracted from plants of the family of the Dictyotales stimulate the golgial and membrane syntheses of glycosaminoglycans of the ECM and the golgial syntheses of proteoglycans of the ECM.

These substances thus increase, for example, the synthesis of collagens, of chondroitin-sulphuric acid, of dermatan-sulphuric acid, of hyaluronic acid . . . .

These substances are used in order to prepare compositions intended for stimulation of the golgial and membrane syntheses of glycosaminoglycans of the ECM and the golgial syntheses of proteoglycans of the ECM. The substances of the present invention are active on the cells of the skin (fibroblasts, keratinocytes), on the cells of the bone (osteoblasts, chondrocytes) and on the cells of the non-osseous articular tissue (synoviocytes). In humans, the ingestion of biologically active substances extracted from plants of the family of the Dictyotales, like the plant in the dried state itself, causes an increase in the synthesis of glycosylated elements of the ECM of the mesenchymal tissues, and more particularly of the skin (dermis and epidermis) and of the bone (cartilage, spongy bone, trabecular bone, connecting cartilage . . . ). The substance extracted from plants of the family of the Dictyotales are thus used in particular in order to prepare pharmaceutical compositions intended for prevention and/or treatment of tissue lesions of the skin, of the bone and of the cartilage. Generally, these substances are used in order to prepare compositions intended for prevention and/or treatment of conditions involving glycosylated elements of the extracellular matrix of animal and human tissues.

The Applicant has demonstrated in his studies that this activity differs from that induced by the majority of activating substances, such as oestradiol and vitamin $D_3$ (1-25-$(OH)_2D_3$), vitamin C etc . . . . The active substance or substances contained in the plants express their activity even in the presence of deleterious agents, such as the interleukins (for example IL-1), and these biologically active substances thus have a repairing activity.

These biologically active substances also have an indirect activity on the cells by acting by the intermediary of messengers, such as a cytokine, a growth factor or a hormone, secreted by the first cell population reached by the active substances extracted from plants and intended for the target cells. The activity of the substances extracted from plants of the family of the Dictyotales is expressed on cells originating from animal species belonging to such diverse branches as the Annelidae, the Ascidiae, the Arthropoda, the molluscs, the bivalves (Conchifera), the Echinodermata, the birds and the mammals. The biologically active substances extracted from plants of the family of the Dictyotales are also used in order to prepare nutritional compositions intended for improving the rearing of Arthropoda and Conchifera, as well as the quality of the shells of eggs.

The substances extracted from plants of the family of the Dictyotales are also of great advantage in bone surgery. In fact, these substances preserve the phenotype of human osteoblasts during grafting and can be inserted with a biomaterial implanted in the vicinity of a joint to regenerate the bone and the articular surfaces. The substances are thus also used in order to prepare compositions intended for prevention and/or treatment of joint conditions.

The substances of the present invention are also used in order to prepare compositions for local use intended for prevention and/or treatment of loco-regional conditions involving glycosylated elements of the extracellular matrix.

The biologically active substances are also used in order to prepare compositions intended for prevention and/or treatment of conditions associated with a degeneration of the extracellular matrix, and also for regeneration of the cartilaginous tissue, or for addition to foods.

The present invention also relates to pharmaceutical, cosmetic and/or nutritional compositions which modify the synthesis of glycosylated elements of the extracellular matrix of animal and human tissues, characterized in that they comprise, as the active principle, one or more biologically active substances extracted from plants of the family of the Dictyotales, in combination or as a mixture with an inert, non-toxic excipient or vehicle suitable for the envisaged use, and if appropriate one or more active principles having a complementary action.

The pharmaceutical, cosmetic and/or nutritional compositions according to the invention are intended for digestive, parenteral, percutaneous, topical or rectal administration. The compositions are thus in the form of non-coated or coated tablets, sugar-coated tablets, capsules, soft gelatine capsules, pills, tablets, sachets, syrups, powders for ingestion or external use, adjuvant compositions for postoperative cicatrization, for burns or traumatisms; suppositories; injectable aqueous solutions or suspensions packaged in ampoules; creams, gels or pomades; or solutions for percutaneous use in a penetrating polar solvent.

The compositions for cutaneous administration but having systemic effects are particularly novel, since it has been demonstrated that under these conditions the biologically active substances extracted from plants of the family of the Dictyotales, when applied to keratinocytes (cutaneous epidermis), were capable for stimulating secretion of a factor by acting on the chondrocytes, the synoviocytes, the osteoblasts and, without doubt, on other mesenchymal cells.

The present invention also relates to implants, characterized in that they comprise, as the active principle, one or more biologically active substances extracted from plants of the family of the Dictyotales, in combination or as a mixture with an inert, non-toxic excipient or vehicle suitable for the envisaged use, and if appropriate one or more active principles having a complementary action.

The following examples and results illustrate the invention. They do not limit it in any way.

EXAMPLE 1
Activity Study of Substances Extracted from Plants of the Dictyotales Family 1) Activity Study An activity study has been achieved on all fractions susceptible to be isolated during a high performance liquid chromatography or a high pression chromatography in order to show that the observed effects are indeed attribuable to biologically active substances specific of plants.

The applicant used two halfquantitative evaluation methods in order to study the activity of these plants. From a tissular or a cellular culture, constituent of the extracellular matrix selected either by immunomarking of cells fixed thanks to its specific antibody; or after cells destruction is detected, a chromatography on gel or an electrophoresis (chromatography under an electric field) with revelation and identification of the substance by specific antobody is achieved.

In both cases, the specific antibody is revelated by a second antibody which is coupled either to a fluorescent molecule, or to an enzyme of which activity underscore a chromophore brought by a substrate.

The relative quantifying can be achieved by picture analysis (immunofluorescence) or by simple spectrophotometry when a coloured substrate is used (Western Blot). When picture analysis is necessary a BIOCOM 200 analyser is used which quantify results from several negatives which have been obtained on several cellular cultures. In every case, values are expressed in relative value (half-quantitative evaluation) in relation to a control and/or in relation to the total quality of the synthetized proteins. The half-quantitative evaluation enable results to be compared between each other. Nevertheless, it is not possible to compare the synthesis of a component to another therefore because of the affinity of antibodies which, although specifics they are, is not the same for two antigen-antibody couples. Results are comparable between each other for a same antibody.

Matricial synthesis of isolated cells have been studied from tissues fragments taken off during surgery operations. Cultures have been achieved in monolayer primary culture and results have been confirmed by three-dimensional cellular cultures. Cultures of tissular fragments, skin, joints, bones provide the same results.

2) Results

Results are expressed by a number corresponding to the detected signal value.

In the following tables, <<BAS>> letters indicate biologically active substances extracted from plants of the dictyotales family.

Dermatan sulfuric acid synthetized by human fibroblasts in a monolayer primary culture:

|  | Average | Standard deviation |
| --- | --- | --- |
| Fibroblasts in a control medium | 32 | 0.54 |
| Fibroblasts with a medium with BAS added | 625 | 21.87 |

Hyaluronic acid synthetized by human fibroblasts in a monolayer primary culture:

|  | Average | Standard deviation |
| --- | --- | --- |
| Fibroblasts in a control medium | 75 | 0.67 |
| Fibroblasts with a medium with BAS added | 428 | 52.10 |

Chondroïtin sulfuric acid synthetized by human chondrocytes in a monolayer primary culture:

|  | Average | Standard deviation |
| --- | --- | --- |
| Control chondrocytes | 56 | 0.85 |
| Chondrocytes with BAS | 445 | 19.45 |

Hyaluronic acid synthetized by human chondrocytes in a monolayer primary culture:

|  | Average | Standard deviation |
| --- | --- | --- |
| Control chondrocytes | 58 | 17 |
| Chondrocytes with BAS | 108 | 21 |

3) Activity Control

This control have been achieved in accordance with litterature indications concerning three-dimensional culture. There, an alginic acid gel has been used.

Chondroïtin sulfuric acid synthetized by human chondrocytes in a three-dimensional culture:

|  | Average | Standard deviation |
| --- | --- | --- |
| Control chondrocytes | 37 | 7 |
| Chondrocytes with BAS | 94 | 8 |

Hyaluronic acid synthetized by human chondrocytes in a three-dimensional culture:

|  | Average | Standard deviation |
| --- | --- | --- |
| Control chondrocytes | 48 | 36 |
| Chondrocytes with BAS | 151 | 50 |

Quite similar results have been obtained with osteoblasts cultures collected from bone samples on diverse varieties of mammalians.

Furthermore, in order to confirm this result, biologically active substances extracted from plants of the Dictyotales family have been applied to tissular cultures of normal or damaged cartilages. It has been noted that a damaged cartilage was poor in synthesis, and in its reserves in glycosaminoglycans of the sulfate chondroïtin and hyaluronic acid types. A damaged cartilage treated by biologically active substances, extracted from plants of the Dictyotales family, has shown greater synthesis rates than the healthy control, untreated by active substances.

4) Pharmacological Action of the Biologically Active Substances

Pharmacological action of the biologically active substances extracted from plants of Dictyotales family is objectived by:

a) Healing activities of the substances in the presence of a deleterious inhibitory agent of the extracellular matrix.

b) Indirect action of substances via a messenger such as a cytokin, a growth factor or an hormone.

Nowadays, litterature agrees to describe most of arthrosic phenomenons as a result of degeneration of the articular areas.

a) Healing activities

The therapeutic activity of a substance is envisaged through the possibility of responding to the deleterious action of a biological intervener responsible for the pathological process. Interleukin 1 (IL-1) is the largest physiological intervener.

That's the reason why, the activity of biologically active substances extracted from plants of the Dictyotales family have been evaluated on the production of glycosaminoglycans elaborated by mesenchymateous cells cultivated in the presence of IL-1.

Cultures Results in the Presence of IL-1

Hyaluronic acid synthetized by human fibroblasts in a monolayer culture:

|  | Average | Standard deviation |
|---|---|---|
| Fibroblasts cultivated in the presence of IL-1 | 36 | 9 |
| Fibroblasts cultivated in the presence of IL-1 and BAS | 451 | 50 |

Dermatan sulfuric acid on chondroïtin sulfuric acid synthetized by human fibroblasts in a monolayer culture:

|  | Average | Standard deviation |
|---|---|---|
| Fibroblasts cultivated in the presence of IL-1 | 14 | 9 |
| Fibroblasts cujtivated in the presence of IL-1 and BAS | 632 | 17 |

Hyaluronic acid synthetized by human osteoblasts in a monolayer culture:

|  | Average | Standard deviation |
|---|---|---|
| Fibroblasts cultivated in the presence of IL-1 | 38 | 1 |
| Fibroblasts cultivated in the presence of IL-1 and BAS | 232 | 5 |

Chondroïtin hyaluronic acid synthetized by human osteoblasts in a monolayer culture:

|  | Average | Standard deviation |
|---|---|---|
| Fibroblasts cultivated in the presence of IL-1 | 28 | 5 |
| Fibroblasts cultivated in the presence of IL-1 and BAS | 280 | 12 |

Hyaluronic acid synthetized by human chondrocytes in a three-dimensional culture:

|  | Average | Standard deviation |
|---|---|---|
| Fibroblasts cultivated in the presence of IL-1 | 78 | 16 |
| Fibroblasts cultivated in the presence of IL-1 and BAS | 125 | 17 |

Chondroïtin sulfuric acid synthetized by human chondrocytes in a three-dimensional culture:

|  | Average | Standard deviation |
|---|---|---|
| Fibroblasts cultivated in the presence of IL-1 | 25 | 3 |
| Fibroblasts cultivated in the presence of IL-1 and BAS | 470 | 21 |

The same kind of results have been obtained with cellular types as well in explants cultures. Half-quantitative evaluation with explants is difficult because section plans must be taken in account.

1) Indirect Action

The applicant noted that, surprisingly, incubated cells with the biologically active substances (BAS) extracted from plants of the Dictyotales family were susceptible to transmitt the signal to other cells, which signal was detected by the latter at the contact with biologically active substances. These biologically active substances thus can stimulate the secretion of a second messenger. This messenger reaches other cellular types and stimulate proteoglycans synthesis.

In order to underscore this phenomenon, tests have been realized in the following manner.

To a keratinocyte culture (human epidermis cells), the biologically active substances have been added in the culture medium. After several hours of incubation, cells are rinsed several times in order to eliminate the rest of biologically active substances (BAS). Then, a new medium (KEM or Mac Coy for example) without foetal calf or animal serum is added. After a new incubation, this medium is reuptaken. The conditionned medium thus obtained is lyophilized. The lyophilizate is reuptaken then diluted at 1/40 or 1/10 by the specific medium wherein it operate the second culture (DMEM for fibroblasts, Mac Coy for osteoblasts for example). Cells cultures treated by the conditionned medium issued from keratinocytes, increase proteoglycans synthesis in the same proportions that if they had been treated themselves directly by biological active substances while those incubated in the presence of a conditionned medium by keratinocytes, but not incubated by biologically active substances, pratically don't have modified their synthesis.

Furthermore, response to the conditionned medium varies depending on whether the lyophilizate reuptaking before dilution is made with alcohol or with an aqueous medium.

In some experimental conditions, osteoblasts show a best response when the medium conditionned by keratinocytes is reuptaken by alcohol, while the same treatment, between fibroblasts on one hand and osteoblasts on the other hand, produces a better response if the lyophilizate is reuptaken directly by medium. It leads to suppose that messengers secreted by cells and producing a same signal for a same population, are different. This test allows the applicant to envisage the possibility for modifying the synthesis of proteoglycans from tissues deeper than skin, by application of a composition, which contains active components, on skin keratocytes or on epthelial tissues.

EXAMPLE II

Compositions

1) As an example, one of the following extracts (which contain the biologically active substances) can be prepared.

| Dryed plant | 200 g |
|---|---|
| Cyclohexane | 1000 g | or:

| Dryed plant | 200 g |
|---|---|
| Ethanol | 1000 g |

Fixation of the extract which contain biologically active substances (BAS) on a support:

| Organic solution | 200 g |
|---|---|
| Hydroxypropylmethylcellulose | 1000 g |

The organic solution is evaporated on the cellulose derivative support
or:

| Organic solution | 20 g |
|---|---|
| Polyethyleneglycol (P.E.G.) 4000 or 6000 | 1000 g | the organic solution is distillated in liquid or solid PEG. Organic solution support ratios vary greatly and are linked to the wanted effect (mass effect, delayed formulation, in situ action, general systemic action, etc.)

2) General use Composition

Capsules and tablets formulations, wherein active substances are extracted with ethanol and fixed on an inert support, turns out to be simplest one. In order to do it, biologically active substances extracted with ethanol are mixed with microcrystalline cellulose, with a lubricating agent such as talc, and with a compressive adjuvant such as glycerol behenate.

Capsules are achieved by using the absorbate of biologically active substances extracted with ethanol, fixed on polyethyleneglycol 4 000 or 6 000 and diluted with colloïdal silica of the Aerosil(R) or Sippernat(R) type.

Transcutaneous way is classically formulated, with or without a tank, and with classical excipients of the Transcutol(R) type.

Injectable way is conceivable with purified biologically active substances which are made dissolved in a suitable liquid for injection in a solution or in a suspension.

Formulation Examples a) Capsules based on biologically active substances (BAS) extracted from plants of the Dictyotales family

| BAS fixed on polyethyleneglycol 6000 | 95% |
|---|---|
| Silica | 5% |

Capsules filling is made as usual.

b) Tablets based on biologically active substances (BAS) extracted from plants of the Dictyotales family:

| BAS fixed on cellulose | 25% |
|---|---|
| Cellulose | 65% |
| Talc | 1.5% |
| Glycerol behenate | 8.5% |

Preferred compositions for pharmaceutical use are forms which can be administered orally such as tablets, dragees, capsules, which contain as active ingredient at least one biologically active substance extracted from plants of the Dictyotales family or adsorbate of biologically active substances on an inert support, in conjunction or admixed with inert, not toxic, suitable for pharmaceutical use diluent or carrier, and eventually one or several active ingredients having a complementary action.

For alimentary use, biologically active substances extracted from plants of the Dictyotales family will be diluted in a nutritive alimentary support such as a meal, or inert such as cellulose or a cellulose rich preparation.

These compositions concern notably shellfishes breeding, and for example shrimps.

Example Shrimps

| BAS | 12.1 |
|---|---|
| Dulectin | 23.9 |
| Calcium carbonate | 5.0 |
| Asperella | 1.0 |
| Wheat germ powder | 54.05 |
| Sippernat | 3.95 |

This formulation, administered at a dose of 1.5 kg during a month to a basin of 180 000 shrimps, has permitted an improvement of hatching survival and an increase of the animal weight, at maturity of 10%±2%.

So, biologically active substances can improve animals medium weight and/or grow shorter the time of maturation.

A similar experiment on laying hens showed that the number of broken eggs during the second cycle of laying was reduced of 2%.

3) Loco-regional use Compositions

Implants use (pellets: small tablets placed under skin) is already classical. It founds is large applications in substitutive hormonal treatment. It allows a prolonged treatment. Putting in by the surgical way biomaterials such as synthetic polymers (polylactic acid, polyacrylic acid), minerals: hydroxyapatite, calcium phosphate, biomaterials: mother-of-pearl, coral . . . impregnated of active ingredients consisting in the biologically active substances extracted from plants of the Dictyotales family is envisaged and doubtless leads to interesting results on the stimulation of proteoglycan systhesis of the extracellular matrix.

4) Topical Compositions Destined for Application with a General, Dermatologic or Cosmetic Aim For the cosmetical or dermatological use, creams or gels will be preferably used, of which use in the field is the most convenient and effective. Without being restrictive, these formulations use emulsions of the oil in water or water in oil type. These emulsions are designated as lotions, day or night creams, in some applications of the cosmetological field and in dermatological applications, ointments, gels, gel-cream mixed formulations.

As an example, an emulsion formulation can be cited; these formulations contain all at least three constituants: water, fatty bodies, emulsifying or tensio-active agents. Obviously, other substances such as colouring agents, texture agents, active ingredients associated or not, preservatives, stabilizing agents of pH, of oxidation, can intervene in the final formula. Ointments are formulations which group together only lipophilic agents. Gels are compositions having a diaphaneous appearance wherein water and sometimes lipophilic components (or silicone) are in a colloïd or a colloïdal suspension state.

Concentrations in biologically active substances (BAS) can vary in great proportions, which range between 0.01 and 20% of the emulsion mass, where 0.01% is the threshold dose. It can also be envisaged the use of encapsulated forms of biologically active substances (liposomes, nanospheres, nanocapsules . . . ) because these are susceptible to improve activity. With 20% of active ingredient, it is necessary to noticeably modify the formulation, the activity being probably at a plateau level.

Modern forms of formulation resorted to gels. Lots of them are formulated with the aid of polymers derivated from acrylic acid described under the name of carbomers. Other types of molecules can lead to gels such as cellulose and its derivatives, colloïdal silicas, uronic acid polymers, mannans, galactomannans, xanthan gums, etc . . . .

EXAMPLE

Oil in Water Cream which Contain Active Substances Extracted with Ethanol Dryed Beforehand

| | |
|---|---|
| Tefose 2000 ® | 11 |
| Lanoline wax | 3.5 |
| Geteol ® | 3.5 |
| Water | 76.7 |
| Preservative | qs |
| BAS (solubie in water) | 5.0 |
| Flavour | 0.3 |
| BAS under vesicular form (liposomes . . . ) | 0.5 |
| Carbomer | 0.5 |
| Solution of NaOH (10%) | QSpH 6.5 |
| Water | QSP 100 ml |
| Preservative, colouring agent | |

It is obviously possible to contemplate other formulations in topical, pharmaceutical and cosmetical applications, such as sponges, patches with local effects, powders, sticks (lipstick) . . . .

What is claimed is:

1. A biologically-active composition to stimulate synthesis of glycosylated elements of extracellular matrix of an animal or human tissues, containing as the active ingredient at least one biologically active substance extracted from plants of the family of Dictyotales which are defined by the following analytical data:

retention times by semi-preparative high performance liquid chromatography on a diol grafted silica support and with an eluent of hexane/isopropanol in the ratio 92:8 ranging from 20 to 25 minutes and from 35 to 40 min;

a retention time by semi-preparative high performance liquid chromatography on the $C_{18}$ grafted silica support and with an eluent of acetonitrile/water in the ratio 85:15, ranging from 15 to 17 minutes;

retention times by semi-preparative high performance liquid chromatography on the $C_{18}$ grafted silica support and with an eluent of acetonitrile/water/acetic acid in the volume volume ratio 85:15:0.05 ranging from 17 to 20 minutes and 30 to 40 minutes; a retention time by high pressure chromatography on a column filled with normal silica and with an eluent of heptane/ether (90:10) ranging from 6.9 minutes to 8.5 minutes;

a retention time by high performance liquid chromatography fitted with $C_{18}$ grafted silica column using an eluent made of methanol/water 80/20, ranging from 16 to 18 minutes; and a pharmaceutically acceptable carrier or excipient.

2. A biologically-active composition of claim 1 having an UV spectrum in methanol showing several absorption bands located at 202 nm with a shoulder at 228 nm, between 260 and 270 nm, between 400 and 460 nm and at 630 nm by a TLC showing after chemical revelation (anisaldehyde-sulfuric acid, vanillin-sulfuric acid, phophomolybdate sulfuric acid/ethanol), frontal retention times of 15.90 and 0.95.

* * * * *